United States Patent
Ali et al.

(10) Patent No.: US 7,049,343 B2
(45) Date of Patent: May 23, 2006

(54) SUBSTITUTED HYDRAZINE DERIVATIVES

(75) Inventors: Syed M. Ali, Solon, OH (US); Kurt R. Brunden, Aurora, OH (US); Dario Doller, Branford, CT (US); Brian Herbert, Streetsboro, OH (US); Jack B. Jiang, Orange Village, OH (US); Amy Jordan, Parma, OH (US)

(73) Assignee: Merck & Co., Inc., Rahway, NJ (US)

( * ) Notice: Subject to any disclaimer, the term of this patent is extended or adjusted under 35 U.S.C. 154(b) by 169 days.

(21) Appl. No.: 10/344,966

(22) PCT Filed: Sep. 7, 2001

(86) PCT No.: PCT/US01/28095

§ 371 (c)(1),
(2), (4) Date: Aug. 28, 2003

(87) PCT Pub. No.: WO02/19967

PCT Pub. Date: Mar. 14, 2002

(65) Prior Publication Data

US 2004/0039025 A1 Feb. 26, 2004

Related U.S. Application Data

(60) Provisional application No. 60/231,010, filed on Sep. 8, 2000.

(51) Int. Cl.
*A01N 74/34* (2006.01)
*A61K 31/175* (2006.01)
(52) U.S. Cl. .................. 514/583; 564/148; 564/310
(58) Field of Classification Search .................. 564/1, 564/100, 103, 106, 112, 113, 148, 310; 514/75, 514/76, 583
See application file for complete search history.

(56) References Cited

U.S. PATENT DOCUMENTS 6,103,743 A  8/2000  Bell et al.

FOREIGN PATENT DOCUMENTS

| WO | WO 97/45115 A1 | 12/1997 |
| WO | WO 97/45423 A1 | 12/1997 |
| WO | WO 99/34790 A1 | 7/1999 |
| WO | WO 99/44596 A2 | 9/1999 |
| WO | WO 99/45011 A1 | 9/1999 |

OTHER PUBLICATIONS

Feiring et al., Macromolecules, 1993, 26, 2779-2784.*
Kaiser et al., Interaction of carbanions with azobenzene and related compounds, J. Org. Chem.; 1972; 37(3); 490-494.*
Beak et al., [1-(Phenylthio)-2-carbamoylallyl]lithium reagents. Electrophilic substitution and formal anionic 3+2 cyclization-elimination, J. Org. Chem.; 1987; 52(2); 218-225.*
Database CAPLUS on CAS Online Printout, AN 1994:289832, Hiramatsu et al. "Probucol scavenged 1,1-diphenyl-2-picrylhydrazyl radicals and inhibited formation of thiobarbituric acid reactive substances". Free Radical Biol. Med., 1994 16(2), 201-6.

* cited by examiner

*Primary Examiner*—Johann Richter
*Assistant Examiner*—Chukwuma Nwaonicha
(74) *Attorney, Agent, or Firm*—J. Eric Thies; Melvin Winokur

(57) ABSTRACT

A method for the inhibition of high affinity glycine transporters, compounds that inhibit these transporters; pharmaceutically active compositions comprising such compounds; and the use of such compounds either as above, or in formulations for the control or prevention of disease states in which glycine is involved are disclosed.

5 Claims, No Drawings

SUBSTITUTED HYDRAZINE DERIVATIVES

This application claims the benefit of Provisional Application No. 60/231,010 filed Sep. 8, 2000.

FIELD OF THE INVENTION

This invention is directed generally to substituted hydrazine derivatives and pharmaceutically acceptable salts thereof. The compounds are inhibitors of high affinity glycine transporters and are thus useful in treating neurological disorders including schizophrenia, dementia, epilepsy, muscle spasticity, mood disorders, learning disorders, neurodegenerative diseases and pain.

BACKGROUND OF THE INVENTION

Glycine acts as a neurotransmitter at two distinct receptor systems. In the spinal cord and certain non-cerebral brain regions, glycine acts much like GABA (γ-amino-n-butyric acid) in causing the opening of an inhibitory Cl$^-$ channel. This activity is mediated by the "strychnine-sensitive" glycine receptor. Glycine also acts as a co-agonist at the NMDA (N-methyl-D-aspartate) glutamate receptor that is localized in the cognitive centers of the brain, including the cortex, hippocampus, and basal ganglia. This receptor has received considerable attention from the pharmaceutical industry since there is compelling evidence that it plays a critical role in learning and cognition. Furthermore, excessive stimulation of the NMDA receptor appears to be responsible for much of the neuronal damage that occurs after stroke-injury and brain trauma. Hence, there are ongoing research efforts to develop both agonists (for increased cognition) and antagonists (for treatment of stroke) to the NMDA receptor.

Recent data suggest that agonists and antagonists to the glutamate site of the NMDA receptor can cause relatively severe side-effects. For example, NMDA antagonists have been shown to cause agitation, hallucinations, and paranoia in stroke patients. Agonists to the glutamate binding site on NMDA receptors have the potential of causing excessive calcium influx and excitotoxic cell damage. In contrast, the glycine site on the NMDA receptor appears to play a modulatory role, and therefore compounds interacting with this site do not appear to evoke such severe side-effects.

Demonstration that Glycine Modulation Improves Cognition

Evidence that molecules acting at the glycine site of the NMDA receptor can effectively enhance receptor activity is provided by several studies showing that glycine agonists or partial agonists are cognitive enhancers in vivo. D-cycloserine, a molecule that crosses the blood-brain barrier and which is a partial agonist at the NMDA glycine site, increased the performance of rats in a learning task model. In fact, D-cycloserine was reported to improve the implicit memory performance in a word recall test in Alzheimer's disease patients. However, because D-cycloserine is only a partial agonist at the glycine site, it may be more useful as an antagonist to the NMDA receptor.

A larger number of studies have been performed with the glycine prodrug, milacemide. This molecule (2-N-pentylaminoacetamide HCl) readily crosses the blood-brain barrier and is metabolized by monoamine oxidase B (MAO-B) to glycinamide. The latter is converted to glycine, which then acts at the NMDA receptor. Milacemide improved the performance of rats in a passive-avoidance task and reversed drug-induced amnesia. This compound has also been shown to improve performance in the Morris water maze task and to increase word retrieval skills in young and elderly healthy human adults. Unfortunately, the effectiveness of the drug wanes after continuous administration because the compound leads to irreversible inactivation of MAO-B, thus blocking the drug's own metabolism. Nonetheless, the data obtained with this compound and D-cycloserine demonstrate that increasing the occupancy of the glycine site of the NMDA receptor results in enhanced cognitive performance in animals and humans without side-effects.

The NMDA Receptor in Schizophrenia

The general view has been that schizophrenia primarily results from hyperfunctioning of the dopaminergic system. The typical anti-psychotics, such as thorazine and haloperidol, are relatively potent dopamine D2 receptor antagonists. In fact, there is a general correlation between clinical efficacy of the classical anti-psychotics (or neuroleptics) and their affinity for the D2 receptor. Further evidence of the importance of the dopaminergic system in schizophrenia is provided by studies showing that dopamine agonists, or agents that increase dopamine levels (like amphetamines), induce psychotic behavior.

While the role of dopamine in schizophrenia is well established, there are compelling reasons to believe that the disorder does not result solely from hyperfunctioning of this neurotransmitter system. For example, although amphetamine-induced psychosis includes certain "positive" symptoms such as delusions, hallucination and agitation, common "negative" aspects of schizophrenia, including emotional withdrawal and mental retardation, are not observed. Perhaps the best indication that the dopamine hypothesis is an over-simplified explanation of schizophrenia is the observation that individuals who have taken excessive phencyclidine (PCP) are clinically indistinguishable from schizophrenics. PCP acts as a selective noncompetitive blocker of the glutamate NMDA receptor at concentrations that induce psychosis, with no apparent effect on dopamine binding. Interestingly, PCP and ketamine (another NMDA channel-blocker) also exacerbate the psychosis of schizophrenic patients, whereas the psychomimetic effects of amphetamine are reduced in schizophrenics. These data imply that schizophrenia results from glutamate hypoactivity in addition to dopamine hyperfunction. Since most schizophrenic patients have some form of information processing deficit also implies that NMDA receptor function may be compromised in this disorder.

Although the available anti-psychotics primarily affect dopaminergic neurotransmission, there is some evidence that they may also have a modest effect on the glutaminergic system. Both haloperidol and clozapine cause an ~40% increase in NMDA receptor activity in vitro at concentrations at which clinical efficacy is seen. Thus, some of their anti-psychotic activity may result from action on the NMDA receptor. The most compelling demonstration of glutamate hypofunction in schizophrenia would be clinical evidence that NMDA agonists improve patient outcome. Small clinical studies have been performed with D-cycloserine, and initial indications are that the compound may improve the negative symptoms and cognitive deficits of schizophrenia. That effects are seen with this partial agonist suggests that full glycine agonists may be particularly efficacious. Of particular interest are clinical studies in which schizophrenics were treated with large oral doses of glycine or placebo. Even though glycine does not penetrate the blood-brain barrier effectively, the patients receiving the glycine treatment showed a statistically significant decrease in negative schizophrenic symptoms.

Modulation of NMDA Receptor Activity Trough Inhibition of Glycine Transporters An approach to enhancing NMDA receptor action is to increase glycine concentrations at the synaptic cleft by inhibiting its removal. While regulation of the transporters for the biogenic amines has been extensively studied, relatively little is known about the types of molecules that inhibit the glycine transporters.

Both astrocytes and neurons are involved in glycine removal. Astrocytic glycine uptake systems have been partially characterized in vitro and in vivo. The high-affinity glycine transporters that are involved in synaptic regulation have been cloned, and two separate genes appear to encode for these transporters. These proteins belong to the same transporter family as those for the biogenic amines, with transport function being both sodium- and chloride-dependent. The GlyT1 glycine transporter is expressed by astrocytes in the spinal cord, brainstem, and brain hemispheres. Isoforms resulting from mRNA splice variants have been described for both GlyT1 and GlyT2, although the physiological significance of these isoforms is not known. The GlyT2 uptake system is restricted to the spinal cord, brainstem and cerebellum, and is not found in the cortex and other regions of the brain hemispheres. Based on their distributions, it is believed that GlyT2 is involved in regulating glycine that acts at the strychnine-sensitive glycine receptors, whereas GlyT1 is likely involved in removing glycine from synapses containing NMDA receptors.

The selective inhibition of GlyT1 action would appear to be a rational approach to increasing the function of the NMDA receptor without the inherent side-effects associated with modulation of the glutamate binding site. Such an approach could provide useful therapeutic agents to treat, for example, schizophrenia, dementias, learning impairment and various neurodegenerative disorders. The inhibition of GlyT2 would lead to elevated levels of glycine near the strychnine-sensitive glycine receptors. The enhancement of activity at this receptor could prove beneficial in treating muscle spasticity resulting, for example, from spinal cord injury or multiple sclerosis. Furthermore, GlyT2 inhibitors might provide benefit in the management of chronic pain.

Known glycine transporter inhibitors include substituted amines (U.S. Pat. No. 6,103,743, WO99/34790, WO97/45115 and 45423) and piperazinyl derivatives (WO99/44596 and 45011). Pyrazoles and pyrazolines are classes of compounds that are of pharmaceutical value and have been described, for example, as treatments for inflammatory disorders (EP178035, EP127371). However, pyrazolidines have not been described as pharmaceutical agents. Furthermore, hydrazines are a known class of compounds that have exhibited biological activities. No hydrazines, however, have been reported to have glycine transporter activities. Substituted hydrazines of Formula I are novel compounds which inhibit glycine transporters.

BRIEF SUMMARY OF THE INVENTION

The invention is directed to novel compounds of Formula I as follows:

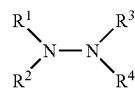

Formula I wherein $R^1$ and $R^4$ are each independently an aryl group; and $R^2$ and $R^3$ are each independently selected from the group consisting of hydrogen, alkyl, alkenyl, alkynyl, alkoxy, alkenoxy, alkynoxy, aliphatic acyl, —$C_1$–$C_3$ alkylamino, alkenylamino, alkynylamino, di($C_1$–$C_3$ alkyl)amino, —C(O)O—($C_1$–$C_3$ alkyl), —C(O)NH—($C_1$–$C_3$ alkyl), —CH═NOH, —C(O)N($C_1$–$C_3$ alkyl)$_2$, haloalkyl, alkoxycarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkenyl, aralkyl, alkylheterocyclyl, heterocyclylalkyl, —$SO_2$—($C_1$–$C_3$ alkyl), —$SO_3$—($C_1$–$C_3$ alkyl), sulfonamido, carbamate, aryloxyalkyl, carboxyl, —C(O)NH(benzyl) and —$(CH_2)_t R^5$;

wherein $R^5$ is selected from the group consisting of hydrogen, amino, hydroxy, alkoxy, aliphatic acyl, —CN, carboxyl, carboxamide, alkoxycarbonyl, —C(O)NHOH, —C(O)NHNH$_2$ and carboxaldehyde; and t is an integer of one to four;

wherein $R^1$, $R^2$, $R^3$, $R^4$ and $R^5$ are unsubstituted or substituted with at least one electron donating or electron withdrawing group;

and wherein $R^2$ and $R^3$ taken together may form a ring; and pharmaceutically acceptable salts thereof.

In preferred compounds of Formula I above, $R^1$ and $R^4$ may each be phenyl, $R^3$ may be hydrogen, alkyl, alkenyl, alkynyl, aliphatic acyl, haloalkyl or —$(CH_2)_t R^5$; and $R^2$ may be hydrogen, alkyl, alkenyl, alkynyl, cycloalkyl or aryl.

More specifically, the compounds of this invention may be described by Formula II below

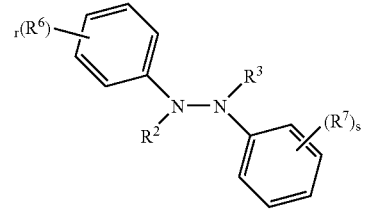

Formula II wherein r and s are each independently an integer of one to five;

$R^6$ and $R^7$ at each occurrence are each independently selected from the group consisting of halogen, alkenyl, alkynyl, alkoxy, aliphatic acyl, —$CF_3$, —$NO_2$, —CN, —C(O)O—($C_1$–$C_3$ alkyl), —C(O)NH—($C_1$–$C_3$ alkyl), —CH═NOH, —$PO_3H_2$, —$OPO_3H_2$, —C(O)N($C_1$–$C_3$ alkyl)$_2$, haloalkyl, carboxaldehyde, carboxamide, aryl, aroyl, biaryl, heterocyclyl, heterocycloyl, aralkenyl, aralkyl, heterocyclylalkyl, sulfonyl, —$SO_2$—($C_1$–$C_3$ alkyl), —$SO_3$—($C_1$–$C_3$ alkyl), sulfonamido, carbamate, aryloxyalkyl, carboxyl and —C(O)NH(benzyl); and $R^2$ and $R^3$ are each independently selected from the group consisting of hydrogen, alkyl, alkenyl, alkynyl, alkoxy, alkenoxy, alkynoxy, aliphatic acyl, —$C_1$–$C_3$ alkylamino, alkenylamino, alkynylamino, di($C_1$–$C_3$ alkyl)amino, —C(O)O—($C_1$–$C_3$ alkyl), —C(O)NH—($C_1$–$C_3$ alkyl), —CH═NOH, —C(O)N($C_1$–$C_3$ alkyl)$_2$, haloalkyl, alkoxycarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkenyl, aralkyl, alkylheterocyclyl, heterocyclylalkyl, —SO$_2$—(C$_1$–C$_3$ alkyl), —SO$_3$—(C$_1$–C$_3$ alkyl), sulfonamido, carbamate, aryloxyalkyl, carboxyl, —C(O)NH(benzyl) and —(CH$_2$)$_t$R$^5$;

wherein R$^5$ is selected from the group consisting of hydrogen, amino, hydroxy, alkoxy, aliphatic acyl, —CN, carboxyl, carboxamide, alkoxycarbonyl, —C(O)NHOH, —C(O)NHNH$_2$ and carboxaldehyde; and t is an integer of one to four;

wherein R$^2$, R$^3$, R$^5$, R$^6$ and R$^7$ are unsubstituted or substituted with at least one electron donating or electron withdrawing group;

and wherein R$^2$ and R$^3$ taken together may form a ring;

and pharmaceutically acceptable salts thereof.

In preferred compounds of Formula II above, r may be an integer of one to three; s may be an integer of one or two; R$^3$ may be hydrogen, alkyl, alkenyl, alkynyl, aliphatic acyl, haloalkyl or —(CH$_2$)$_r$R$^5$; R$^2$ may be hydrogen, alkyl, alkenyl, alkynyl, cycloalkyl or aryl; and, R$^6$ and R$^7$ may each independently be halogen, alkenyl, alkynyl, aliphatic acyl, —CF$_3$, —NO$_2$, —CN, —C(O)O—(C$_1$–C$_3$ alkyl), —C(O)NH—(C$_1$–C$_3$ alkyl), alkoxy, —C(O)N(C$_1$–C$_3$alkyl)$_2$, aryl, aroyl, —SO$_2$—(C$_1$–C$_3$ alkyl), —SO$_3$—(C$_1$–C$_3$ alky) or sulfonamido.

More specifically, the compounds of this invention may be described by Formula III below

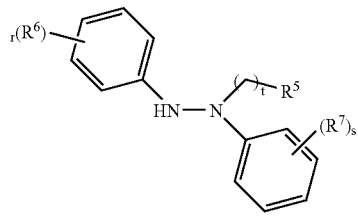

Formula III wherein r is an integer of one to three;

s is an integer of one or two;

t is an integer of one to four;

R$^6$ and R$^7$ at each occurrence are each independently selected from the group consisting of halogen, alkenyl, alkynyl, aliphatic acyl, —CF$_3$, —NO$_2$, —CN, —C(O)O—(C$_1$–C$_3$ alkyl), —C(O)NH—(C$_1$–C$_3$ alkyl), alkoxy, —C(O)N(C$_1$–C$_3$ alkyl)$_2$, aryl, aroyl, sulfonyl, —SO$_2$—(C$_1$–C$_3$ alkyl), —SO$_3$—(C$_1$–C$_3$ alkyl) and sulfonamido; and R$^5$ is selected from the group consisting of hydrogen, amino, hydroxy, alkoxy, aliphatic acyl, —CN, carboxyl, carboxamide, alkoxycarbonyl, —C(O)NHOH, —C(O)NHNH$_2$ and carboxaldehyde;

wherein R$^5$, R$^6$ and R$^7$ are unsubstituted or substituted with at least one electron donating or electron withdrawing group; and pharmaceutically acceptable salts thereof.

In preferred compounds of Formula III above, r is three and s is one.

Presently preferred compounds include 3-(N'-(2,6-dinitro-4-trifluoromethylphenyl)-N-(3-methoxyphenyl)hydrazino)propionic acid, 3-(N'-(2,6-dinitro-4 trifluoromethylphenyl)-N-(3-methoxyphenyl)hydrazino)propiontrile, 3-(N'-(2,6-dinitro-4-trifluoromethylphenyl)-N-phenylhydrazirio)-N-hydroxypropionamide, 2-[N'-(2,6-Dinitro-4-trifluoromethylphenyl)-N-phenylhydrazino]-N-hydroxyacetamide and pharmaceutically acceptable salts thereof.

Useful derivatives of the compounds of Formulae I, II and III include esters, carbamates, aminals, amides, optical isomers and prorugs thereof.

The present invention also relates to a pharmaceutical composition comprising a compound of Formula I, in a pharmaceutically acceptable carrier.

The present invention also relates to a method for selectively inhibiting glycine transporters in a mammal comprising administering to said mammal a therapeutic amount of a compound of Formula I.

DETAILED DESCRIPTION OF THE INVENTION

Definitions of Terms

The term "alkyl" as used herein alone or in combination refers to C$_1$–C$_{12}$ straight or branched, substituted or unsubstituted saturated chain radicals derived from saturated hydrocarbons by the removal of one hydrogen atom, unless the term alkyl is preceded by a C$_x$–C$_y$ designation. Representative examples of alkyl groups include methyl, ethyl, n-propyl, iso-propyl, n-butyl, sec-butyl, iso-butyl, and tert-butyl, among others.

The term "alkenyl", alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl", alone or in combination, refers to a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" refers to a C$_1$–C$_6$ unit for a particular functionality. For example lower alkyl means C$_1$–C$_6$ alkyl.

The term "alkylaryl" alone or in combination, refers to an aryl group substituted with at least one alkyl radical.

The term "aliphatic acyl" alone or in combination, refers to radicals of formula alkyl-C(O)—, alkenyl-C(O)— and alkynyl-C(O)— derived from an alkane-, alkene- or alkyncarboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl and methylpropiolyl, among others.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. "Cycloalkyl" includes cis or trans forms. Furthermore, the-substituents may either be in endo or exo positions in the bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkynyl" as used herein alone or in combination refers to a cyclic carbocycle containing from 4 to 8 carbon atoms and one or more triple bonds.

The term "cycloalkylalkyl" as used herein refers to a cycloalkyl group appended to a lower alkyl radical, including, but not limited to cyclohexylmethyl.

The term "halo" or "halogen" as used herein refers to I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy", alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkoxycarbonyl", alone or in combination, refers to an alkoxy group as previously defined appended to the parent molecular moiety through a carbonyl group. Examples of alkoxycarbonyl groups include methoxycarbonyl, ethoxycarbonyl and isopropoxycarbonyl among others.

The term "alkenoxy", alone or in combination, refers to a radical of formula alkenyl-O—, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy", alone or in combination, refers to a radical of formula alkynyl-O—, provided that the radical is not an -ynol ether. Examples of suitable alkynoxy radicals include, but are not limited to, propargyloxy, 2-butynyloxy and the like.

The term "carboxyl" as used herein refers to a carboxylic acid radical, —C(O)OH.

The term "thioalkoxy", refers to a thioether radical of formula alkyl-S—, wherein "alkyl" is as defined above.

The term "sulfonamido" as used herein refers to —SO$_2$NH$_2$.

The term "carboxaldehyde" as used herein refers to —C(O)R wherein R is hydrogen.

The term "carboxamide" as used herein refers to —C(O) NR$_a$R$_b$ wherein R$_a$ and R$_b$ are each independently hydrogen, alkyl or any other suitable substituent.

The term "alkoxyalkoxy" as used herein refers to R$_c$O—R$_d$O— wherein R$_c$ is lower alkyl as defined above and R$_d$ is alkylene wherein alkylene is —(CH$_2$)$_{n'}$— wherein n' is an integer from 1 to 6. Representative examples of alkoxyalkoxy groups include methoxymethoxy, ethoxymethoxy, t-butoxymethoxy among others.

The term "alkylamino" as used herein refers to R$_e$NH— wherein R$_e$ is a lower alkyl group, for example, ethylamino, butylamino, among others.

The term "alkenylamino" alone or in combination, refers to a radical of formula alkenyl-NH— or (alkenyl)$_2$N—, wherein the term "alkenyl" is as defined above, provided that the radical is not an enamine. An example of such alkenylamino radical is the allylamino radical.

The term "alkynylamino", alone or in combination, refers to a radical of formula alkynyl-NH— or (alkynyl)$_2$N— wherein the term "alkynyl" is as defined above, provided that the radical is not an amine. An example of such alkynylamino radicals is the propargyl amino radical.

The term "dialkylamino" as used herein refers to R$_f$R$_g$N— wherein R$_f$ and R$_g$ are independently selected from lower alkyl, for example diethylamino, and methyl propylamino, among others.

The term "amino" as used herein refers to H$_2$N—.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, and isopropoxycarbonyl among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group selected from the group consisting of furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" employ the term "alkyl" as defined above. Rings may be multiply substituted.

The term "aralkyl", alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "aralkenyl", alone or in combination, refers to an aryl substituted alkenyl radical, wherein the terms "aryl" and "alkenyl" are as defined above.

The term "arylamino", alone or in combination, refers to a radical of formula aryl-NH—, wherein "aryl" is as defined above. Examples of arylamino radicals include, but are not limited to, phenylamino(anilido), naphthylamino, 2-, 3-, and 4-pyridylamino and the like.

The term "aryloxyalkyl" as used herein refers to an arylether radical attached to an alkyl group.

The term "biaryl", alone or in combination, refers to a radical of formula aryl—aryl, wherein the term "aryl" is as defined above.

The term "thioaryl", alone or in combination, refers to a radical of formula aryl-S—, wherein the term "aryl" is as defined above. An example of a thioaryl radical is the thiophenyl radical.

The term "aroyl", alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocyclyl", alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "alkylheterocyclyl" as used herein refers to an alkyl group as previously defined appended to the parent molecular moiety through a heterocyclyl group.

The term "heterocyclylalkyl" as used herein refers to a heterocyclyl group as previously defined appended to the parent molecular moiety through an alkyl group.

The term "heterocycloyl", as used herein refers to radicals of formula heterocyclyl-C(O)—, wherein the term "heterocyclyl" is as defined above. Examples of suitable heterocycloyl radicals include tetrahydrofuranylcarbonyl, piperidinecarbonyl and tetrahydrothiophenecarbonyl among others.

The term "aminal" as used herein refers to a hemi-acetal of the structure $RCH(NH_2)(OH)$.

The term "amide" as used herein refers to a moiety ending with a —$C(O)NH_2$ functional group.

The term "ester" as used herein refers to —$C(O)R_m$, wherein $R_m$ is hydrogen, alkyl or any other suitable substituent.

The term "carbamate" as used herein refers to compounds based on carbamic acid, $NH_2C(O)OH$.

The term "optical isomers" as used herein refers to enantiomers which are optically active.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkytheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O)O—. Rings may be substituted multiple times.

When $R^2$ and $R^3$ are taken together to form a ring, the ring formed may be heterocyclyl or aryl, as defined above. An example of such ring formation is found in compound 23 of Table 1.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in *Advanced Organic Chemistry* by J. March, 1985, pp. 16–18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, and aryl lower alkanoyl among others. Electron donating groups include-such groups as hydroxy, lower-alkyl; amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio and alkyldithio.

As used herein, the term "composition" is intended to encompass a product comprising the specified ingredients in the specified amounts, as well as any product which results, directly or indirectly, from a combination of the specified ingredients in the specified amounts.

Abbreviations

Abbreviations which have been used in the schemes and the examples which follow are: DEAD for diethylazodicarboxylate, EDCI for 1-(3-diethylaminopropyl)-3-ethylcarbodiimide, HOBt for 1-hydroxybenzotriazole hydrate, DMF for dirnethyl formamide, THF for tetrahydrofuran, and TLC for thin layer chromatography.

Examples of procedures that may be used to synthesize compounds of the formulae shown above are presented in the following Schemes.

The synthesis of the compounds of the invention is illustrated in Scheme I. An N-substituted pyrazolidinone (1) reacts with a substituted halobenzene in the presence of a base, such as n-butyl lithium or sodium hydride, in a solvent such as N,N-dimethyl formamide, N-methylpyrrolidinone, tetrahydrofuran or dimethyl sulfoxide, to afford the substituted pyrazolidinone 2, which is then treated with a nucleophile HX to form compounds of Formula I. For example, when compound 2 is treated with ammonia, the ring-opened carboxylic amide 3 of Formula I is formed, which can be further converted to the nitrile 4 of Formula I.

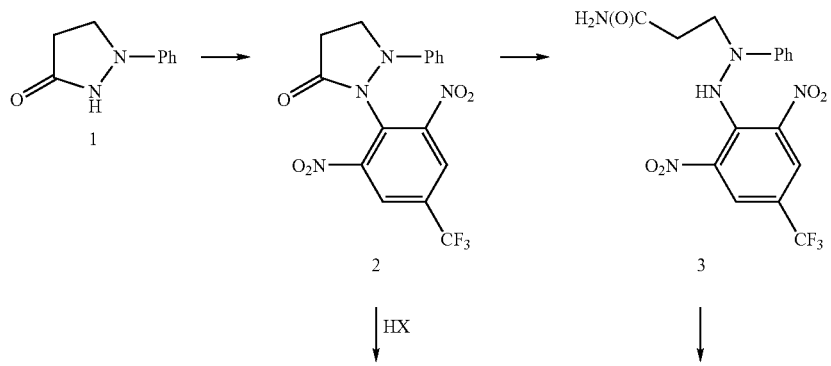

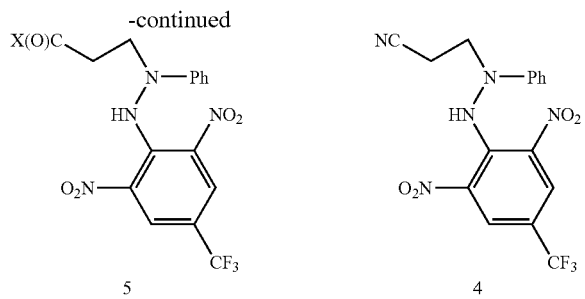

An alternative synthesis is depicted in Scheme II. An aminopyrazoline 6 reacts with a substituted halobenzene in the presence of a base, such as n-butyl lithium or sodium hydride, in a solvent such as N-methyl formamide, N-methyl pyrrolidinone, or dimethyl sulfoxide, to afford the nitrile 4 of Formula I.

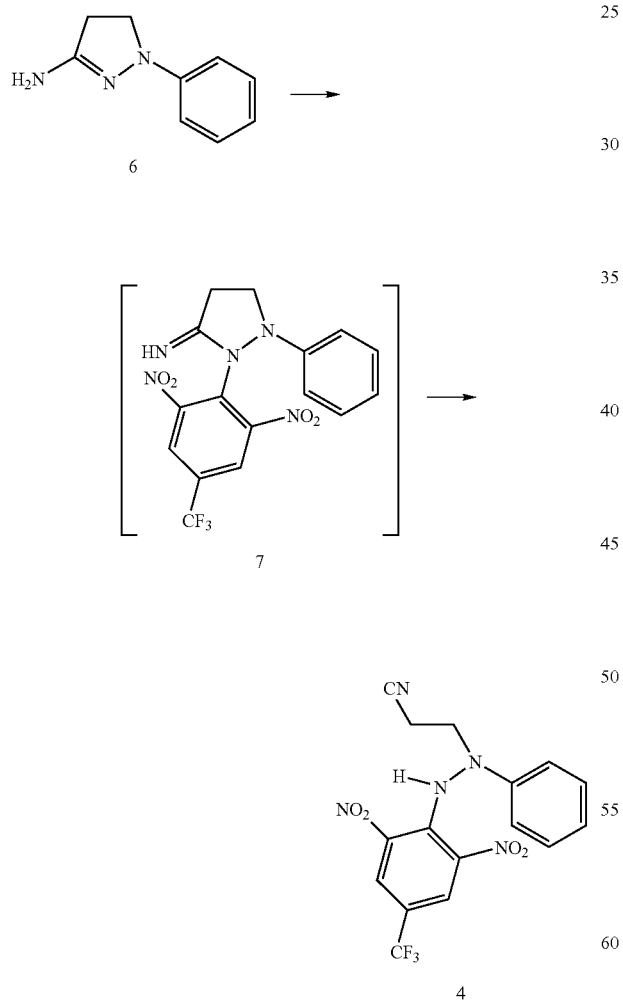

The nitrile group in 4 may further be changed into other functional groups, such as carboxylic group via hydrolysis, amino group via reduction, or amidine group via amination.

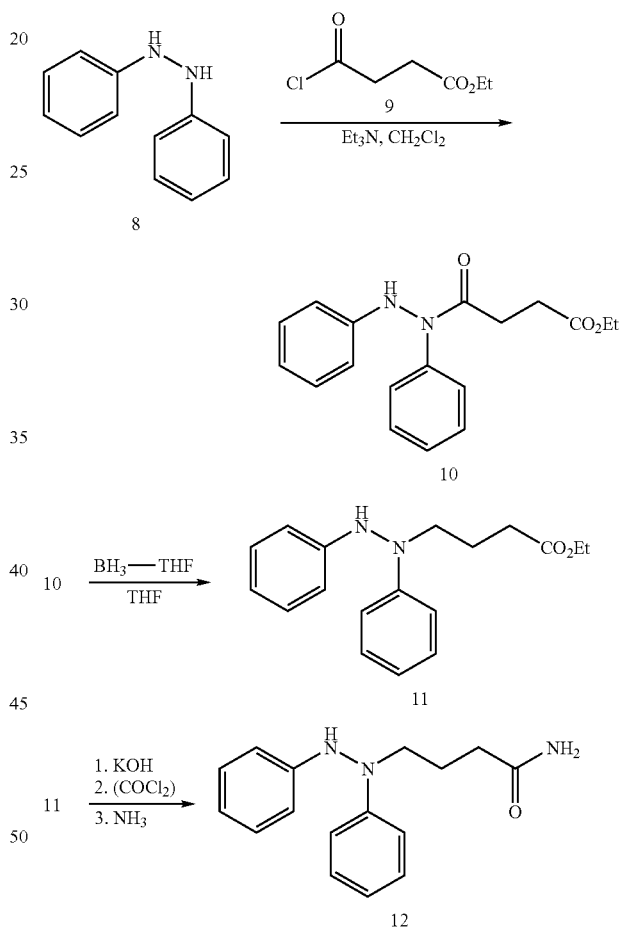

The synthesis of analogs devoid of functionality of the aromatic rings is outlined in Scheme III above. The reaction of diphenyl hydrazine (8) with an acid chloride 9 such as ethyl succinyl chloride, provided the corresponding amide 10 in good yield. Removal of the amide was accomplished by a selective reduction in the presence of the ester using $BH_3$.THF. Ester 11 was subsequently transformed into a variety of functional groups using standard procedures. As depicted in Scheme III, ester 11 was transformed into amide 12 via saponification followed by acid chloride formation and quenching with ammonia.

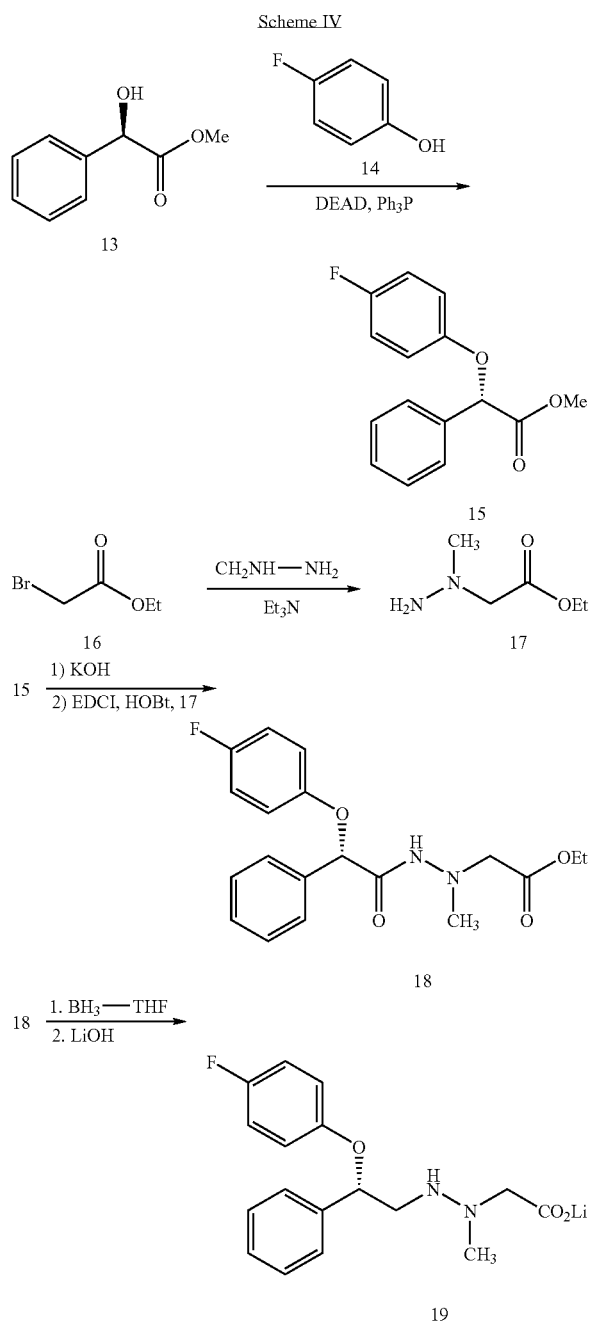

The synthesis of non-aromatic substituted hydrazines such as 19 is detailed in Scheme IV. The synthetic strategy is convergent and begins with the simple preparation of both fragments 15 and 17. The unification of ester 15 and hydrazine 17 can be mediated by trimethylaluminum, in accord with the Weinreb procedures, *Tet. Let.* No. 48, pp. 4171–4174, 1977. Selective reduction of amide 18 followed by saponification completed the synthesis.

A detailed description of the preparation of representative compounds of the present invention is set forth in the Examples.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences,* 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable, base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethyl ammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, or the like.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery. Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Proper fluidity can be maintained, for example, by the use of coating materials such as lecithin, by the maintenance of the required particle size in the case of dispersions and by the use of surfactants.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfiryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

The present invention contemplates both synthetic compounds of Formulae I, II and III of the present invention, as well as compounds formed by in vivo conversion to compounds of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The ability of compounds of the present invention to inhibit GlyT1 activity is described in detail hereinafter in the Examples. These Examples are presented to describe preferred embodiments and utilities of the invention and are not meant to limit the invention unless otherwise stated in the claims appended hereto.

EXAMPLE 1

2-(2,6-Dinitro-4-trifluoromethylphenyl)-1-phenylpyrazolidin-3-one (Compound 2 in Table 1) was synthesized according to the following procedure, illustrated by general Scheme I.

1-Phenylpyrazolidin-3-one (1.01 g, 6.23 mmol) was added to a suspension of NaH (6%, 278 mg, 6.95 mmol, 1.1 eq.(equivalents)) in DMF (31 mL) under a blanket of $N_2$ at ambient temperature. After 30 minutes, 4-chloro-3,5-dinitrobenzotrifluoride (2.00 g, 7.39 mmol, 1.2 eq.) was added to the red solution. The reaction mixture was maintained for 12 hours and was then poured onto H₂O (120 mL) and extracted with Et₂O/CH₂Cl₂ [(2/1) 3×50 mL]. The combined organic layers were dried (Na₂SO₄) and concentrated in vacuo. The residue was purified by chromatography (hexanes/EtOAc, 4/1) to provide the title product (2.21 g, 89%) as a yellow-orange foam.

EXAMPLE 2

3-[N'-(2,6-Dinitro-4-trifluoromethylphenyl)-N-phenylhydrazino]propionamide (Compound 3 of Table 1) was synthesized according to the following synthetic procedure, illustrated by general Scheme I.

Concentrated ammonium hydroxide (3.5 mL) was added to a solution of 2-(2,6-Dinitro-4-trifluoromethylphenyl)-1-phenylpyrazolidin-3-one (502 mg, 1.27 mmol) in THF (8 mL). The reaction mixture darkened to a deep brown within 20 seconds. After 10 minutes, brine (20 nL) was added and the mixture extracted with CH₂Cl₂ (3×10 mL). The combined organic layers were dried (Na₂SO₄) and concentrated in vacuo. The residue was purified by chromatography [hexanes/EtOAc, 2/1 (300 mL) then 1/4] to give the title product as a red foam (493 mg, 94%).

EXAMPLE 3

3-[N'-(2,6-Dinitro-4-trifluoromethylphenyl)-N-phenylhydrazino]propionitrile (Compound 4 of Table 1) was synthesized according to the following procedure, illustrated by general Scheme I.

A solution of 3-[N'-(2,6-Dinitro-4-trifluoromethylphenyl)-N-phenylhydrazino]pionamide (79 mg, 0.19 mmol) in dry benzene (3 mL) was treated with dry dimethylformamide (0.1 mL, 1.29 mmol, 6.8 eq.) and thionyl chloride (0.17 mL, 2.3 mmol, 12 eq.) at room temperature. The mixture was stirred for 15 minutes and then slowly diluted with water and extracted with ether. The organic layer was dried (Na₂SO₄) and concentrated in vacuo to provide the crude title product (80 mg). A pure sample of the title product was obtained as yellow needles by purification by preparative TLC (hexane/EtOAc, 2/1) followed by recrystallization from hexanes.

EXAMPLE 4

3-[N'-(2,6-Dinitro-4-trifluoromethylphenyl)-N-phenylhydrazino]propionitrile (Compound 4 of Table 1) was alternatively synthesized according to the following procedure, illustrated by general Scheme II.

A solution of the aminopyrazoline 6 (1.24 mmol) in dry N,N-dimethylformamide (3 mL) was treated with sodium hydride (50 mg, 1.24 mmol) at 0° C. The mixture was stirred at 0° C. for 1 hour followed by the addition of a solution of the substituted chlorobenzene (1.36 mmol) in N,N-dimethylformamide (2 mL). The reaction mixture was stirred at room temperature for 4 hours and treated with water. The resulting mixture was extracted with ethyl acetate, and the organic layer was separated, washed with water and dried over anhydrous Na₂SO₄ to afford a crude product, which was purified by flash column chromatography to provide the final product 4 of Formula 1.

EXAMPLE 5

3-(N,N'-Diphenylhydrazinocarbonyl)propionic acid ethyl ester (Compound 10 of Table 1) was synthesized according to the following procedure, illustrated in Scheme III.

A solution of diphenyl hydrazine (1.01 g, 5.48 mmol) and triethylamine (0.80 mL, 5.7 mmol, 1 equivalent) in dry methylene chloride (9 mL) was treated dropwise with ethyl succinyl chloride (0.85 mL, 6.0 mmol, 1.1 equivalents) at 0° C. The reaction mixture was allowed to warm to room temperature after five minutes, and then was maintained at that temperature for three hours. The contents of the reaction vessel were then poured into water and the resultant layers were separated. The organic layer was washed (saturated NaHCO₃ and brine), dried over magnesium sulfate and concentrated. The residue was purified by chromatography (4:1 hexane/ethyl acetate) to provide the product (1.45 g, 85% as an oil.

EXAMPLE 6

4-(N,N'-Diphenylhydrazino)butyric acid ethyl ester (Compound 11 of Table 1) was synthesized according to the following procedure, illustrated in Scheme III.

Borane.tetrahydrofuran complex (1.0 M, 0.64 mmol, 2 equivalents) was added dropwise to a 0° C. solution of amide 10 (108 mg, 0.346 mmol) in tetrahydrofuran. After 1.5 hours, the reaction was quenched with methanol (0.8 mL) and concentrated. The residue was purified by PTLC (4:1 hexane:ethyl acetate) to provide the title compound (81.3 mg, 79%) as an oil.

Compounds of Formula I that were synthesized according to the general synthetic procedures are summarized in Table I. The last column in the Table indicates which synthetic scheme the compound was prepared in accordance with. Ph used in the structures in the Table stands for phenyl.

TABLE I

| No. | Structure | Name | ¹H NMR | |
|---|---|---|---|---|
| 2 | 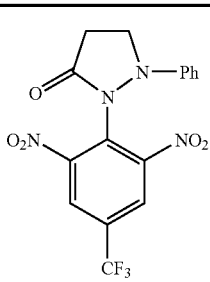 | 2-(2,6-dinitro-4-trifluoromethyl phenyl)-1-phenylpyrazolidin-3-one | 8.10(s, 2H), 7.33–7.28(m, 4H), 7.16–7.12(bm, 1H), 2.90 (t, J=7.2, 2H), 2.85 (t, J=7.5, 2H) | I |

TABLE I-continued

| No. | Structure | Name | ¹H NMR | |
|-----|-----------|------|--------|---|
| 3 | 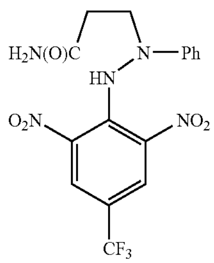 | 3-(N'-(2,6-dinitro-4-trifluoromethyl phenyl)-N-phenylhydrazino) propionamide | 10.44(s, 1H), 8.57 (bs, 1H), 7.69(bs, 1H), 7.29(t, J=7.5, 2H), 7.00(t, J=7.5, 1H), 6.87 (d, J=7.5, 2H), 5.51 (bs, 1H), 5.36(bs, 1H), 3.86–3.79(m, 1H), 3.63(m, 1H), 2.68–2.57(m, 1H), 2.42–2.35(m, 1H) | I |
| 4 | 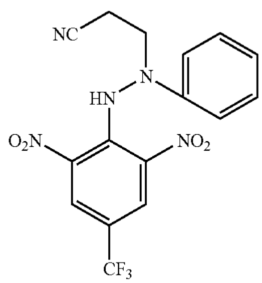 | 3-(N'-(2,6-dinitro-4-trifluoromethyl phenyl)-N-phenylhydrazino) propionitrile | 9.82(s, 1H), 8.00 (bs, 2H), 7.34(t, J=7.5, 2H), 7.10(t, J=7.5), 6.92(d, J=7.8, 2H), 3.77 (bm, 1H), 3.65(bm, 1H), 2.59(bm, 2H) | I, II |
| 10 | 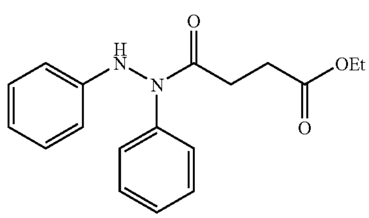 | 3-(N,N'-Diphenyl hydrazino carbonyl)propionic acid ethyl ester | 7.48(m, 2H), 7.30 (m, 2H), 7.22(m, 3H), 6.85(m, 3H), 4.13(q, 2H, J=6.9), 2.89(br m, 2H), 2.66(t, 2H, J=6.0), 1.24(t, 3H, J=7.2) | III |
| 20 | 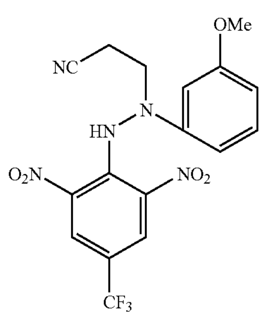 | 3-(N'-(2,6-Dinitro-4-trifluoromethyl phenyl)-N-(3-methoxyphenyl) hydrazino) propionitrile | 9.80(s, 1H), 7.24 (t, J=7.5, 1H), 6.62(d, J=6, 1H), 6.48(d, J=6.3, 1H), 6.44(s, 1H), 3.76(s and bm, 4H), 3.63(bm, 1H), 2.59 (bm, 1H) | I, II |
| 21 | 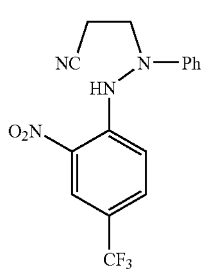 | 3-(N'-(2-Nitro-4-trifluoromethyl phenyl-N-phenyl hydrazino) propionitrile | 9.28(s, 1H), 8.50 (s, 1H), 7.66(d, J=7.2, 1H), 7.55(s, 1H), 7.53(m, J=9, 1H), 7.32(t, J=8.7, 2H), 7.02(t, J=7.5, 1H), 6.96(d, J=7.8, 2H), 3.91(bm, 1H), 3.80(bm, 1H), 2.70 (bm, 2H) | I, II |

TABLE I-continued

| No. | Structure | Name | ¹H NMR | |
|---|---|---|---|---|
| 22 | 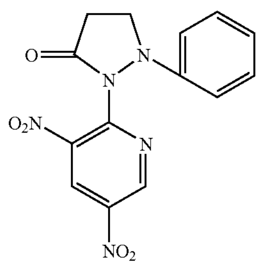 | 2-(3,5-Dinitropyridin-2-yl)-1-phenyl pyrazolidin-3-one | 9.37(d, 1H, J=2.1), 8.97(d, 1H, J=2.4), 7.31(t, 2H, J=8.4), 7.23(d, 1H, J=7.5), 7.09(t, 2H, J=7.2), 4.13(t, 2H, J=7.5), 2.85(t, 2H, J=7.5) | I |
| 23 | 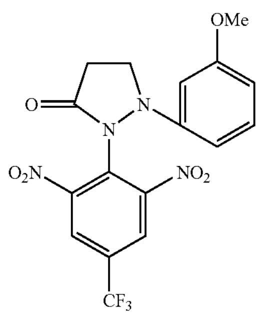 | 2-(2,6-Dinitro-4-trifluoromethyl phenyl)-1-(3-methoxyphenyl) pyrazolidin-3-one | 8.10(s, 2H), 7.21 (t, 1H, J=8.1), 6.99 (t, 2H, J=2.4), 6.83 (dd, 1H, J=7.8, 1.8), 6.66(dd, 1H, J=8.4, 2.4), 3.90(t, 2H, J=7.8), 3.75 (s, 3H), 2.84 (t, 2H, J=7.5) | I |
| 24 | 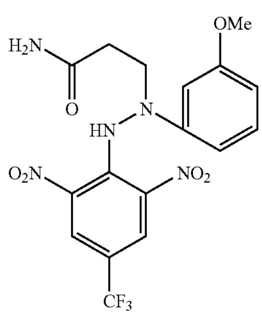 | 3-N'-(2,6-Dinitro-4-trifluoromethyl phenyl)-N-(3-hydrazino) propionamide | 10.51(s, 1H), 8.55 (br s, 1H), 7.69(br s, 1H), 7.18(t, 1H, J=8.4), 6.53(dd, 1H, J=8.4, 2.1), 6.42(m, 3H), 5.52 (br s, 1H), 3.79(m, 1H), 3.64(s, 3H), 3.51(m, 1H), 2.67 (m, 1H), 2.36(m, 1H) | I |
| 25 | 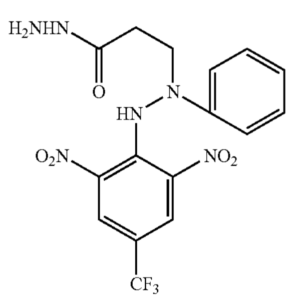 | 3-(N'-(2,6-Dinitro-4-trifluoromethyl phenyl)-N-phenylhydrazino) propionic acid hydrazide | 10.2(s, 1H), 8.56 (br s, 1H), 7.71(br s, 1H), 7.27(t, 1H, J=8.4), 6.99(t, 1H, J=7.5), 6.87(d, 2H, J=7.2), 3.84(m, 1H), 3.57(m, 1H), 2.50(m, 1H), 2.28 (m, 1H) | I |
| 26 | 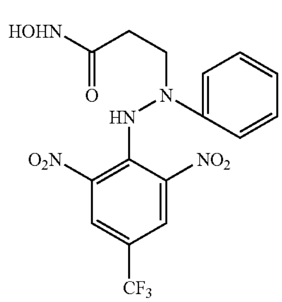 | 3-(N-(2,6-Dinitro-4-trifluoromethyl phenyl)-N-phenyl hydrazino)-N-hydroxy propionamide | 10.27(s, 1H), 9.04 (br s, 1H), 8.49(br s, 1H), 7.67(br s, 1H), 7.22(t, 2H, J=7.5), 6.94(t, 1H, J=7.2), 6.81(d, 2H, J=7.5), 3.81(m, 1H), 3.43(m, 1H), 2.49(m, 1H), 2.26 (m, 1H) | I |

TABLE I-continued

| No. | Structure | Name | ¹H NMR | |
|---|---|---|---|---|
| 27 | 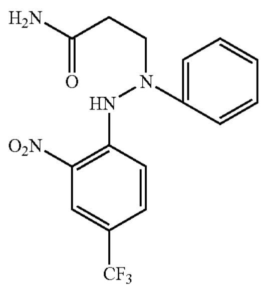 | 3-(N'-(2-Nitro-4-trifluoromethyl phenyl)-N-phenylhydrazino) propionamide | 9.53(s, 1H), 8.47 (s, 1H), 7.58(d, 1H, J=7.2), 7.36(d, 1H, J=9), 7.27(t, 2H, J=8.1), 6.93(m, 3H), 5.80(br s, 1H), 5.43(br s, 1H), 3.91(t, 2H, J=6.3), 2.64(br m, 1H), 2.53(br m, 1H) | I |
| 28 | 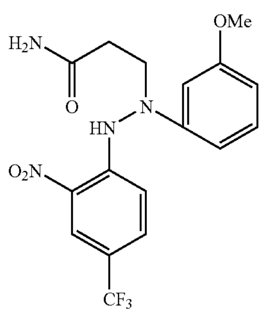 | 3-(N-(3-Methoxyphenyl)-N'-(2-Nitro-4-trifluoromethyl phenyl)-N-phenylhydrazino) propionamide | 9.56(s, 1H), 8.46 (s, 1H), 7.57(d, 1H, J=7.2), 7.33(d, 1H, J=9.0), 7.19(t, 1H, J=9.6), 6.48(m, 3H), 5.84(br s, 1H), 5.47(br s, 1H), 3.90(m, 2H), 2.65(m, 1H), 2.52 (m, 1H) | I |
| 29 | 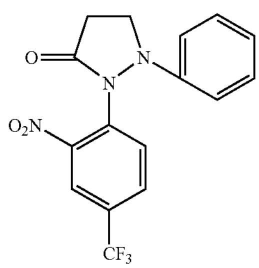 | 2-(2-Nitro-4-trifluoromethyl phenyl)-1-phenyl pyrazolidin-3-one | 8.07(s, 1H), 7.81 (d, 1H, J=8.7), 7.74 (d, 1H, J=7.2), 7.30 (t, 2H, J=7.2), 7.22 (d, 2H, J=7.8), 7.07 (t, 1H, J=7.2), 4.06 (t, 2H, J=7.5), 2.78 (t, 2H, J=7.5) | I |
| 30 | 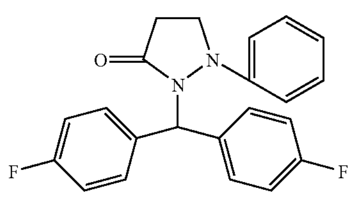 | 2-(Bis-(4-fluorophenyl) methyl)-1-phenylpyrazolidin-3-one | 7.34(m, 4H), 7.02 (m, 6H), 6.88(t, 1H, J=0.9), 6.80(d, 2H, J=7.2), 6.33(s, 1H), 3.85(t, 2H, J=7.5), 2.47(t, 2H, J=7.5) | I |
| 31 | 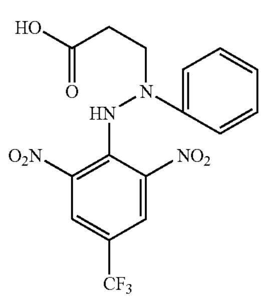 | 3-(N'-(2,6-Dinitro-4-trifluoromethyl phenyl)-N-phenyl hydrazino)propionic acid | 10.02(s, 1H), 8.57 (br s, 1H), 7.73(br s, 1H), 7.31(t, 2H, J=7.5), 7.03(t, 1H, J=7.5), 6.87(d, 2H, J=8.1), 3.82(m, 1H), 3.59(m, 1H), 2.71(m, 1H), 2.57 (m, 1H) | I |

TABLE I-continued

| No. | Structure | Name | ¹H NMR | |
|---|---|---|---|---|
| 32 | 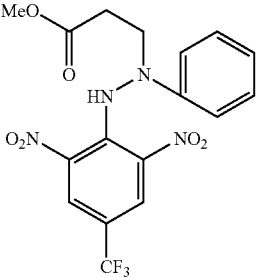 | 3-(N'-(2,6-Dinitro-4-trifluoromethyl phenyl)-N-phenyl hydrazino)propionic acid methyl ester | 9.94(s, 1H), 8.54 (br s, 1H), 7.68(br s, 1H), 7.29(t, 2H, J=8.1), 7.02(t, 1H, J=7.5), 6.88(d, 2H, J=7.8), 3.81(m, 1H), 3.62(s, 3H), 3.58(m, 1H), 2.65 (m, 1H), 2.51(m, 1H) | I |
| 33 | 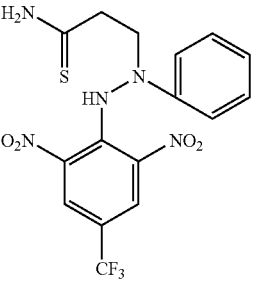 | 3-(N'-(2,6-Dinitro-4-trifluoromethyl phenyl)-N-phenyl hydrazino) thiopropionamide | 9.66,(s, 1H), 8.57 (br s, 1H), 7.75(br s, 1H), 7.44(br s, 1H), 7.31(t, 2H, J=8.4), 7.05(t, 1H, J=7.5), 6.95(d, 2H, J=7.8), 6.85(br s, 1H), 3.96(br m, 1H), 3.86(br m, 1H), 2.86(br m, 1H), 2.79(br m, 1H) | I |
| 34 | 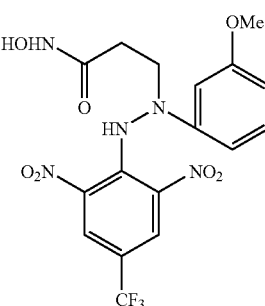 | 3-(N'-(2,6-Dinitro-4-trifluoromethyl phenyl)-N-(3-methoxyphenyl) hydrazino)-N-hydroxy propionamide | 10.29(br s, 1H), 8.49(br s, 1H), 7.68 (br s, 1H), 7.14(t, 1H, J=8.1), 6.48(d, 1H, J=8.4), 6.38(d, 1H), 6.36(s, 1H), 3.77(m, 1H), 3.70 (s, 3H), 3.46(m, 1H), 2.53(m, 1H), 2.27(m, 1H) | I |
| 35 | 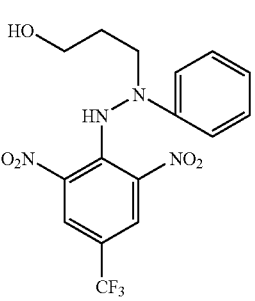 | 3-(N'-(2,6-Dinitro-4-trifluoromethyl phenyl)-N-phenyl hydrazino) propan-1-ol | 10.29(br s, 1H), 8.58(br s, 1H), 7.70 (br s, 1H), 7.29(d, 2H, J=7.5), 6.98(t, 1H, J=7.2), 6.86(d, 2H, J=7.8), 3.75 (m, 4H), 3.26(m, 2H), 1.89(m, 1H) | I |
| 36 | 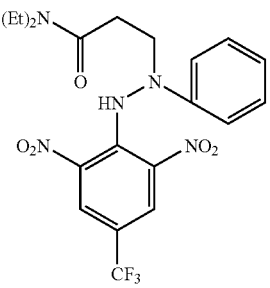 | 3-(N'-(2,6-Dinitro-4-trifluoromethyl phenyl)-N-phenyl diethyl propionamide | 10.52(br s, 1H), 8.56(br s, 1H), 7.68 (br s, 1H), 7.26(t, 2H, J=7.5), 6.97(t, 1H, J=7.5), 6.87(d, 2H, J=8.4), 3.84 (m, 1H), 3.63(m, 1H), 3.29(q, 2H, J=7.2), 3.12(q, 2H, J=7.2), 2.65(m, 1H), 2.45(m, 1H), 1.03 (t 3H, J=7.2), 0.92 (t, 3H, J=7.2) | I |

TABLE I-continued

| No. | Structure | Name | ¹H NMR | |
|---|---|---|---|---|
| 37 | (structure) | (N,N'-Diphenylhydrazino carbonyl)acetic acid methyl ester | 7.54(d, 2H, J=8.1), 7.34(t, 1H, J=7.8), 7.26(t, 4H, J=8.4), 6.93(t, 1H, J=7.5), 6.82(d, 2H, J=7.8), 6.72(s, 1H), 3.74(s, 5H) | III |
| 39 | (structure) | (N'-(2,6-Dinitro-4-trifluoromethyl phenyl)-N-phenylhydrazino) acetic acid ethyl ester | 10.46(s, 1H), 8.66 (br s, 1H), 7.79(br s, 1H), 7.32(t, 2H, J=8.4), 7.07(t, 1H, J=7.5), 6.92(d, 2H, J=8.7), 4.37(d, 1H, J=18), 4.21(q, 2H, J=6.9), 4.04(d, 1H, J=18), 1.27(t, 3H, J=6.9) | I |
| 40 | (structure) | 2-(N'-(2,6-Dinitro-4-trifluoromethyl phenyl)-N-phenylhydrazino)-N-hydroxyacetamide | 10.63(s, 1H), 9.10 (br s, 1H), 8.59(br s, 1H), 7.77(br s, 1H), 7.23(m, 2H), 6.91(m, 3H), 4.13 (q, 3H, J=7.2), 3.91 (d, 1H, J=7.2), 3.91 (d, 1H, J=16.8), 1.27(t, 3H, 3=7.2) | I |
| 41 | (structure) | (N'-(2,6-Dinitro-4-trifluoromethyl phenyl)-N-methylhydrazino) acetic acid methyl ester | 10.07(s, 1H), 8.57 (br s, 1H), 7.83(br s, 1H), 4.29(q, 2H, J=6.9), 3.73(d, 1H, J=18), 3.42(d, 1H, J=18), 2.75(s, 3H), 1.35(t, 3H, J=6.9) | I |
| 42 | (structure) | 3-(N'-(2,6-Dinitro-4-trifluoromethyl phenyl)-N-(3-methoxyphenyl) hydrazino)propionic acid | 10.02(s, 1H), 8.56 (br s, 1H), 7.72(br s, 1H), 7.20(t, 1H, J=8.1), 6.55(d, 1H, J=8.1), 6.44(d, 1H, J=8.1), 6.40(s, 1H), 5.28(s, 1H), 3.80(m, 1H), 3.75 (s, 3H), 3.30(m, 1H), 2.75(m, 1H), 2.58(m, 1H) | I |

TABLE I-continued

| No. | Structure | Name | ¹H NMR | |
|---|---|---|---|---|
| 43 | 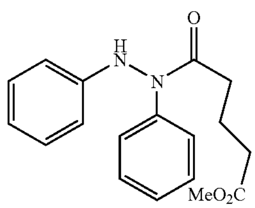 | 4-(N,N'-Diphenyl hydrazino carbonyl)butyric acid methyl ester | 7.47(m, 2H), 7.33 (m, 2H), 7.23(m, 2H), 6.89(t, 2H, J= 6.6), 6.81((m, 2H), 6.60(br s, 1H), 3.63(s, 3H), 2.66(br m, 2H), 2.40(m, 2H), 2.02 (m, 2H) | II I |
| 44 | 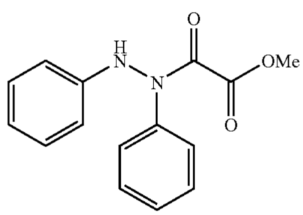 | (N,N'-Diphenyl hydrazino) oxoacetic acid methyl ester | 7.54(d, 2H, J=8.1), 7.35(t, 2H, J=7.2), 7.24(m, 3H), 6.92 (m, 3H), 6.62(s, 1H), 3.77(s, 3H) | II I |
| 46 | 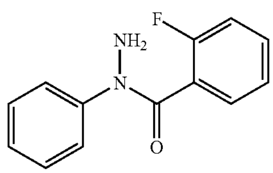 | 2-Fluorobenzoic acid N-phenylhydrazide | 7.21(m, 6H), 6.89 (m, 2H), 4.85(br s, 2H) | II I |
| 51 | 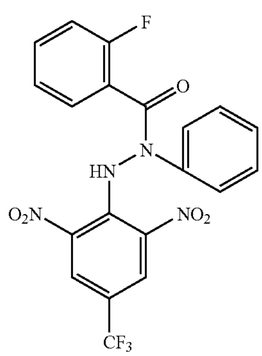 | 2-Fluorabenzoic acid N'-(2,6-dinitro-4-trifluoromethyl phenyl)-N-phenylhydrazide | 10.38(br s, 1H), 8.28(s, 2H), 7.48 (m, 2H), 7.37(m, 2H), 7.25(m, 2H), 7.13(t, 2H, J=7.5), 6.94(t, 1H, J=9.0) | I |

EXAMPLE 5

The ability of compounds to inhibit GlyT1 activity was determined in an assay that utilizes human U373MG astrocytoma cells. The cells were seeded into 96-well plates at $1 \times 10^4$ cells per well in 0.1 ml of culture medium, and were allowed to grow for an additional two days to come to confluence. Prior to the start of transport studies, the cells were washed thoroughly with Kreb's-Ringer phosphate buffer containing 140 mM NaCl, 5 mM KCl and 0.75 mM $CaCl_2$. One set of triplicate wells was washed with chloride-free buffer to serve as a measure of low affinity glycine transport, since high-affinity uptake requires Cl⁻. Test compounds (10 µM) dissolved in fresh buffer, as well as buffer-only controls, were added to the assay plate (50 µl/well). Uptake analyses were initiated by the addition of buffer containing [³H]glycine (0.5 µCi/well), with a final glycine concentration of 100 nM. Glycine uptake was terminated after an 8 minute period by removing the medium and washing the cells with buffer. The cells in each well were subsequently solubilized in detergent to allow scintillation counting of the internalized [³H]glycine. Untreated cells were lysed prior to initiation of the assay for protein determinations, using the BCA assay (Pierce Chemical Company, Rockford, Ill.). Glycine uptake is expressed as mnoles glycine/mg protein/min.

When the compounds of Table 1 are tested according to the above procedure, they are shown to inhibit high-affinity glycine uptake by the astrocytoma cells.

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from nte concept and scope of the invention as defined in the following claims:

We claim:

1. A compound of the structure:

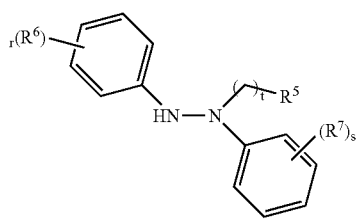

wherein r is an integer of one to three;
s is an integer of one or two;
t is an integer of one to four;
$R^6$ and $R^7$ at each occurrence are each independently selected from the group consisting of: halogen, alkenyl, alkynyl, aliphatic acyl, —$CF_3$, —$NO_2$, —CN, —C(O)O—($C_1$–$C_3$ alkyl), —C(O)NH—($C_1$–$C_3$ alkyl), alkoxy, —C(O)N($C_1$–$C_3$ alkyl)$_2$, aryl, aroyl, sulfonyl, —$SO_2$—($C_1$–$C_3$ alkyl), —$SO_3$—($C_1$–$C_3$ alkyl) and sulfonamido; and $R^5$ is selected from the group consisting of: hydrogen, amino, hydroxy, alkoxy, aliphatic acyl, —CN, carboxyl, carboxamide, alkoxycarbonyl, —C(O)NHOH, —C(O)NHNH$_2$ and carboxaldehyde;

wherein $R^5$, $R^6$ and $R^7$ are unsubstituted, or substituted with at least one electron donating or electron withdrawing group;

or a pharmaceutically acceptable salt thereof.

2. The compound of claim 1 wherein r is three and s is one.

3. A compound which is selected from the group consisting of:

3-(N'-(2,6-dinitro-4-trifluoromethylphenyl)-N-(3-methoxyphenylhydrazino)propionic acid, 3-(N'-(2,6-dinitro-4-trifluoromethylphenyl)-N-(3-methoxyphenyl) hydrazino)propionitrile, 2-[N'-(2,6-dinitro-4-trifluoromethylphenyl)-N-phenylhydrazino]-N-hydroxyacetamide, and 3-(N'-(2,6-dinitro-4-trifluoromethylphenyl)-N-phenylhydrazino)-N-hydroxypropionamide, or a pharmaceutically acceptable salt thereof.

4. A pharmaceutical composition comprising a compound of claim 1 or a pharmaceutically acceptable salt thereof and a pharmaceutically acceptable carrier.

5. A method for the treatment of schizophrenia which comprises administering to a patient in need thereof a therapeutic amount of the compound of claim 1 or a pharmaceutically acceptable salt thereof.

* * * * *